United States Patent [19]

Rothenberg et al.

[11] Patent Number: 4,713,067
[45] Date of Patent: Dec. 15, 1987

[54] URINARY COLLECTION SYSTEM FOR MALE INCONTINENT

[76] Inventors: I. Herbert Rothenberg; Thelma Rothenberg, both of 319 Hill House, Huntingdon Pike, Huntingdon Valley, Pa. 19006

[21] Appl. No.: 876,089

[22] Filed: Jun. 19, 1986

[51] Int. Cl.$^4$ .................................................. A61F 5/44
[52] U.S. Cl. ..................................... 604/353; 604/349; 604/350; 604/351; 24/30.5 R; 292/318; 383/71; 383/96
[58] Field of Search ............... 604/349, 353, 346–348, 604/350–352, 327; 128/760, 767; 4/144.1–144.4; 383/70, 71, 77, 96; 24/30.5 P, 30.5 T, 30.5 R; 292/318

[56] References Cited

U.S. PATENT DOCUMENTS

| | | | |
|---|---|---|---|
| 919,875 | 4/1909 | Johnson | 604/353 |
| 1,064,301 | 6/1913 | Donegan | 383/71 |
| 2,392,034 | 1/1946 | Ellis et al. | 383/96 |
| 2,476,375 | 7/1949 | Kent | 604/353 |
| 2,856,932 | 10/1958 | Griffits | 128/767 |
| 2,940,450 | 6/1960 | Witt et al. | 604/353 |
| 3,559,651 | 2/1971 | Moss | 604/349 |
| 3,631,857 | 1/1972 | Maddison | 604/349 |
| 3,835,857 | 9/1974 | Rogers, III et al. | 604/349 |
| 3,976,076 | 8/1976 | Beach | 604/349 |
| 4,073,295 | 2/1978 | Laufbahn | 604/353 |

FOREIGN PATENT DOCUMENTS

| | | | |
|---|---|---|---|
| 657004 | 2/1963 | Canada | 604/349 |
| 690443 | 7/1964 | Canada | 604/349 |
| 1445658 | 10/1966 | France | 604/327 |
| 324767 | 1/1978 | U.S.S.R. | 604/349 |

*Primary Examiner*—Dalton L. Truluck
*Assistant Examiner*—Mario Costantino
*Attorney, Agent, or Firm*—Ruth Moyerman

[57] ABSTRACT

A body worn urinary collection system for a male incontinent is disclosed. A reusable, generally moisture-proof and pliable penile sheath is shaped as an open-ended sack, and is sized to loosely overfit the male organ. The sack includes an oversized, first resilient, outer ferrule rimming the sack's open end. The cooperation of the ferrule and a strap on the sheath secures the sheath to the male organ with a snug and comfortable dam against backflow and leakage. The sheath may also include a urine outlet proximate the closed sack end to be connected to a urine storage bag via a flexible drain tube. The urine storage bag may be body mounted and includes an outlet orifice with plug means to release the stored urine at a desired time.

21 Claims, 8 Drawing Figures

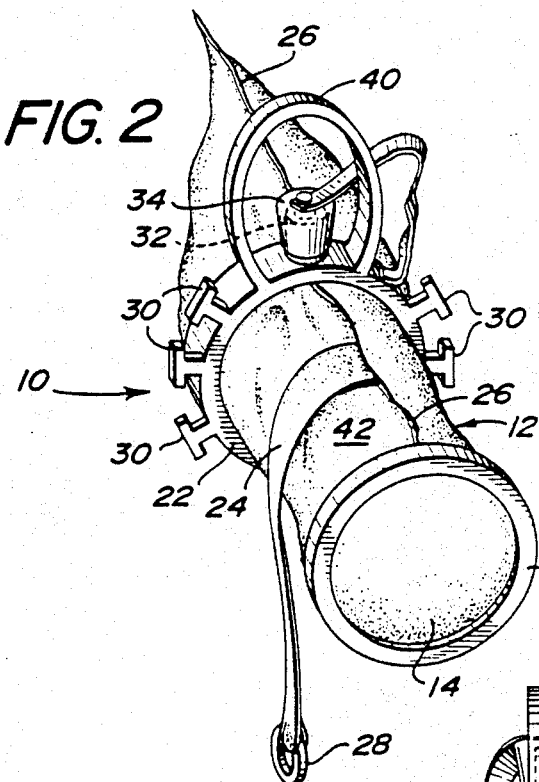
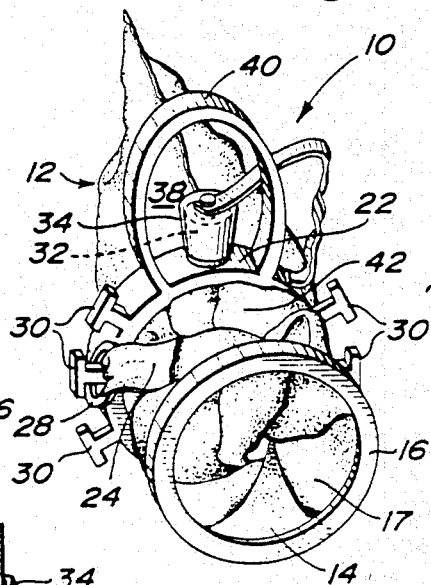
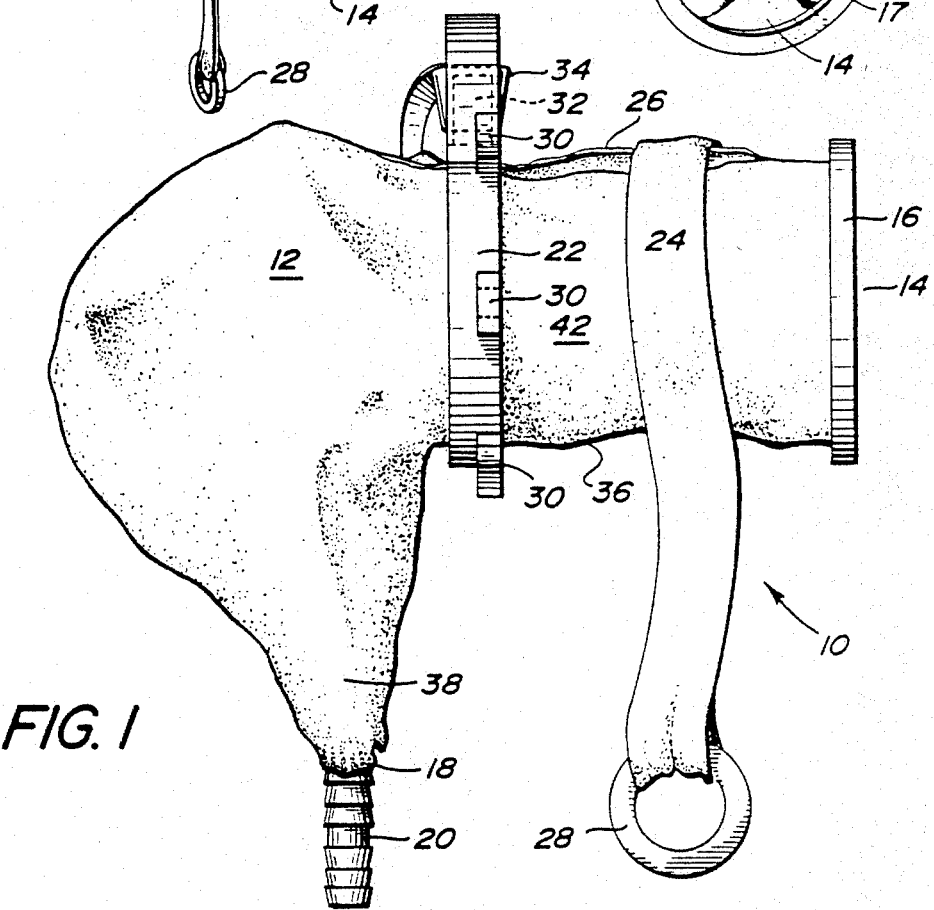

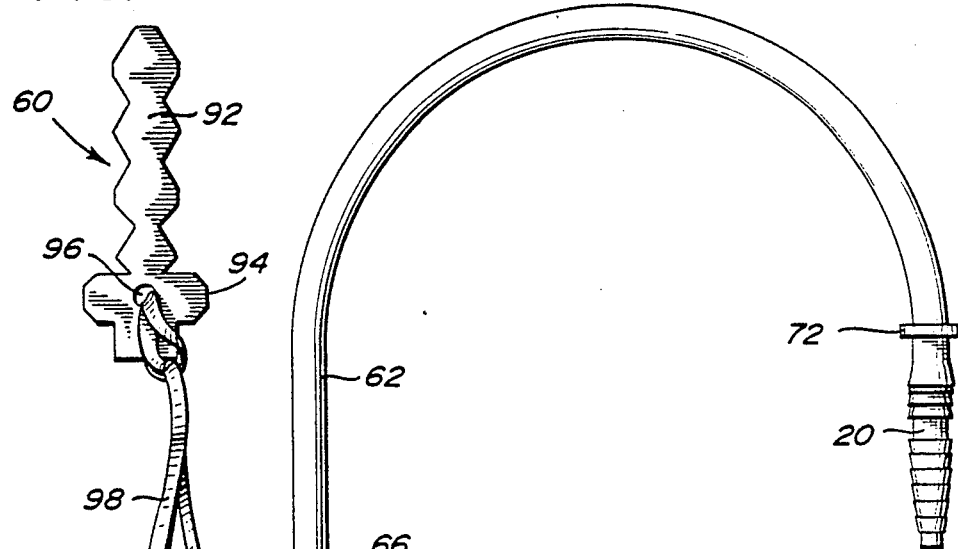
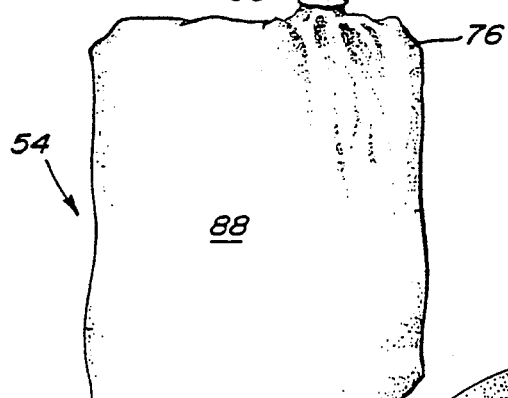
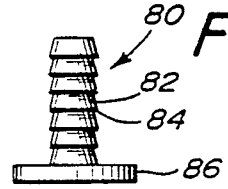
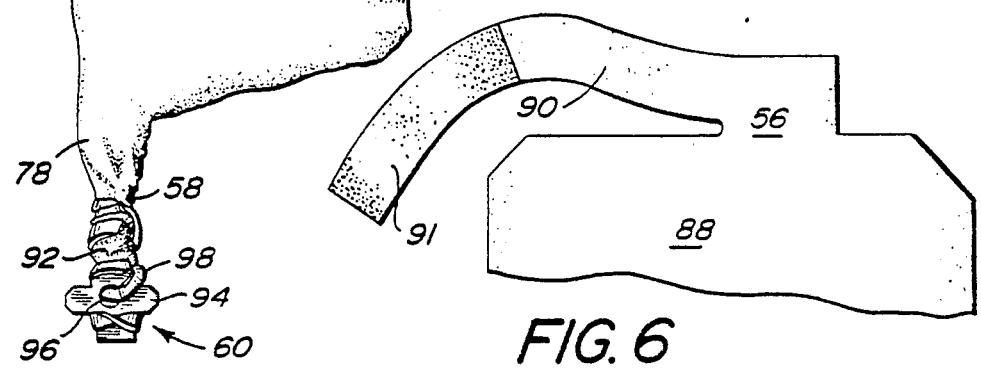

URINARY COLLECTION SYSTEM FOR MALE INCONTINENT

BACKGROUND OF THE INVENTION

1. Field of the Invention

This invention relates to a urinal for male incontinents, and more particularly to a body worn urinal that conforms comfortably to the body.

2. Description of the Prior Art

Disease, injury, birth defects or degenerative processes may result in incontinence of a temporary or permanent nature in a male of any age. One so affected requires a dignified, secure and healthy urine collection system.

A good many devices have been proposed to facilitate the care of incontinence, but the vast majority of these have some limitations which cause them to work inefficiently. To be considered efficient, an apparatus must be easily donned and comfortable enough to permit constant and around-the-clock wear, while still effectively collecting and containing urine without introducing either an added health problem of infection or a socially embrassing presentment.

The prior art apparatuses generally include a urinary external catheter of a condom-like device offered in only three to four fixed sizes and all are incapable of personalization. These are generally retained on the male organ by rigid rings, adhesive material, or a combination thereof. The tight constriction around the penis required to secure the device to the penis can cause discomfort, circulation problems, irritation of the skin, and sometimes serious and permanent damage to penile tissue and function. Likewise, such a configuration causes a backflow problem with the penis continuing to be soaked in the urine, thereby creating a substantial risk of infection. Moreover, most of the devices are suspended from the penis itself, thereby creating troublesome problems.

No device is belived known wherein an easily donned, single sized apparatus to fit any male organ comfortably, yet anugly enough to overcome any backflow problem, is provided. Likewise, no device is known in which there is ventilation and wherein the main body of the penile sheath is held spaced apart and away from the penis, thereby preventing chafing, cramping and the hazards of infection. The sheath's design effects maximum tractability and submission to the contours of the wearer's outer garments, thus eliminating the detectability that results from the molded tubular and kindred prior art devices.

SUMMARY OF THE DISCLOSURE

The aforementioned prior art problems are obviated by the device of this invention in which a body worn, urinary collection system is provided. This invention comprises a reusable, generally moisture-proof and pliable penile sheath shaped as an open-ended, preferably edge seamed sack and sized to generally loosely overfit the male organ. The sheath includes a first oversized, resilient, outer ferrule rimming the open and of the sheath's tunnel to simplify and facilitate comfortably mounting the sheath to the male organ. An adjustable strap means for fastening the device in place is also provided.

In a second embodiment, a second external ferrule with spaced apart cleats and a breather pipe at the top of the ferrule is also provided and is located at and permanently affixed to the terminus of the tunnel preferably behind the quasi-"elephant head" shape of the sheath. This second external ferrule effectively stops folds in the sheath material that result from the gathering of the strapped tunnel material from spreading to and distorting the configuration of the sheath sack, or diminishing its pliability.

Also included as an addition is a replaceable flexible hose which leads from the urine outlet of the sheath to the generally flexible, waterproof and expandable urine storage bag which is attached to the discharge end of the hose in a unique manner which enables instant mounting of the urine bag onto the drain tube. The urine bag is readily and adjustably mounted to either of the user's thighs at the level and circumferential position that assures maximum comfort and minimum interference with the free flow of urine from the sheath to the urine bag, regardless of whether the user is standing, sitting, kneeling or lying prone.

It is therefore an object of this invention to provide an apparatus that prevents malodor and backflow and the risk of anatomical injury, functional impairment and accompanying infection.

It is also an object of this invention to provide an apparatus that fits in any posture of the user, functions effectively and securely, yet provides maximum comfort while eliminating visible and embrassing elevations in the cloth of the user's trouser leg.

It is a further object of this invention to provide one apparatus sized to comfortably fit any male organ and that can be easily and safely mounted and used.

It is yet another object of this invention to provide an apparatus with ventilation to help reduce odor and the risk of embarassment and infection.

It is still another object of this invention to provide a healthful, comfortable, spacious, ventilated hood for the penis as a urine collection aid.

It is also another object of this invention to provide a very economical, discardable urine storage facility that precludes the necessity or impulse to continue the use of expensive urine storage facilities that are overage, noxious and embrassing, or which have become medically unacceptable.

These and other object will be more readily ascertainable to one skilled in the art from a consideration of the following description, Figures and exemplary embodiments.

BRIEF DESCRIPTION OF THE DRAWING(S)

FIG. 1 is a side view of the apparatus of this invention, before mounting, showing the penile sheath including the first outer ferrule at the sheath's open end, retaining strap, and second cleated ferrule at the opposite end of the sheath tunnel.

FIG. 2 is a top and end view of the apparatus of this invention showing details of the cleated ferrule permanently surmounted on the surface of the penile sheath tunnel.

FIG. 3 is the same view of FIG. 2, this view showing the folding pattern of the sheath tunnel as it would appear if it were secured by the strap means to a male organ.

FIG. 4 is a side view of the apparatus of this invention showing the urine storage bag and its orifice mating means.

FIG. 5 is an enlargement view of the apparatus of this invention showing the means to secure the urine storage bag to the drain tube.

FIG. 6 is a partial enlargement view of the apparatus of this invention showing the tether attachment of the urine storage bag.

FIG. 7 is an enlargement view of the apparatus of this invention showing the vent plug.

DETAILED DESCRIPTION OF THE PREFERRED EMBODIMENT(S)

Figure 8:
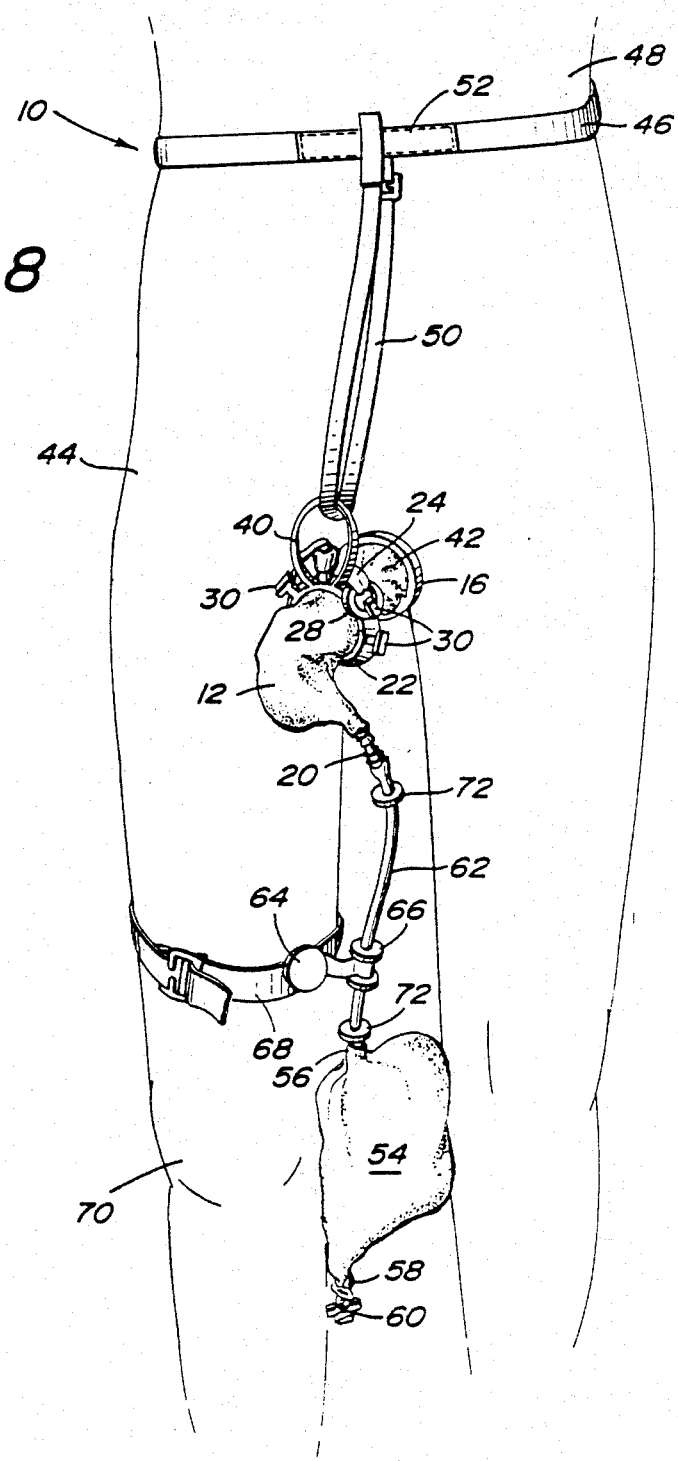
FIG. 8 is a schematic front view of the total assembled apparatus of this invention shown worn by a user.

Referring now to the drawings, and more particularly to FIG. 1, a side view of apparatus 10 shows reusable, generally moistureproof and pliable, "elephant-head shape", penile sheath 12 shaped with open end 14 sized to loosely overfit the male organ. Open end 14 forms the entryway to tunnel 42 which, at the point of cleated ferrule 22, leads into sheath 12. This oversized construction vastly aids the user in mounting or donning the apparatus. First oversized, resilient, outer ferrule 16 rims open end 14. First ferrule 16 is essential to the invention as it gives structure to the mouth of the sheath, aids in donning the device and, as will be explained in reference to FIG. 3, causes the sheath between first ferrule 16 and second cleated ferrule 22 to fold into a definitive space economizing pattern when tightened on the penis by the user as tightly as is comfortable, thus enhancing both the leakproof capacity of the device and the personal endurance factor.

Urine outlet 18 is located proximate the closed sack end and contains mating means 20 adapted to mate with a drain tube (shown and discussed in FIG. 8).

Second cleated ferrule 22 is permanently located at the middle of sheath 12 and forms spacious tunnel 42 for, and entry to, the sack portion of sheath 12. Strap 24 is attached to front rim 26 of sheath 12 between ferrule 16 and cleated ferrule 22. Strap 24 terminates in ring 28, adapted for sizing purposes to engage any one of cleats 30. Breather pipe 32 (shown in phantom), with releasable cap 34, is located atop cleated ferrule 22 with a matching aperture (not shown), thereby providing a ventilating system to reduce odor and lessen the risk of infection.

The elephant-head shape preference of sheath 12 is clearly shown in FIG. 1. In this view, sheath 12 is comprised of two longitudinal halves (one shown) being rim-seamed together, thereby forming front rim 26 and rear rim 36. This seam, while not required, is desirable because it forms a demarcation which, when the apparatus is worn, enhances side-to-side flexibility not attainable in a seamless tubular structure. The closed end of sheath 12 terminates in cone 38, cone 38 being generally at right angles to the main body of sheath 12 so as to house the penis at a comfortable angle and provide a hood which is spaced apart from the penis, a hood design which surrounds but does not grasp or constrict the penis and provides for free circulation of air and thus ventilation. This generally loose construction is very desirable both for comfort and reduction of infection, as it must be appreciated that the device is intended to be worn continuously and/or for long periods of time.

Referring now to FIG. 2, a top and end view of apparatus 10 shows a detail of cleated ferrule 22 on penile sheath 12 including spaced apart cleats 30. Breather pipe 32 (shown in phantom), with its tethered cap 34 and harness 40, are proximate front rim 26. The function of harness 40 will be discussed in FIG. 5.

Strap 24 is attached at its other end to sheath 12 at front rim 26, and terminates at its other end in ring 28. Ferrule 16 at open end 14, and cleated ferrule 22 surrounding penile sheath 12, form the boundaries for tunnel 42 into which the shaft of a penis is to be fitted.

Referring now to FIG. 3, a top and end view of apparatus 10 is again shown but as it would appear if the device were mounted on the penis. The cooperation of ferrule 16 at open end 14 and cleated ferrule 22, as strap 24 is wrapped around the sheath and tightened against the shaft of the penis, is shown. Strap 24 is shown overfitting and secured to cleats 30 by ring 28, and this position of strap 24 creates folds within tunnel 42, allowing for a snug and comfortable dam against backflow. Harness 40 is shown arched over breather pipe 32 (in phantom) and its removable cap 34.

In this view, the aforementioned folding pattern of the mounted and tightened sheath is visible at 17. Thus, it may be seen that the device of this invention is totally adjustable to practically any expectant size male organ and may be loosened or tightened easily by the user until a level of comfort and adequate containment against backflow is obtained. Penile sheath 12 therefore has a built-in sizing capability and eliminates the need to offer sheaths in multiple sizes or shapes. At the same time, due to the interception by cleated ferrule 22, folds from collar 42 are prevented from spreading into cone 38, thereby preventing distortion in the configuration of cone portion 38 of sheath 12, and allowing cone 38 to act as a comfortable, spacious, and ventilated hood for the penis.

Referring now to FIG. 4, urine storage bag 54, which may be provided as part of this apparatus, is shown as preferably a generally rectangular shape with intake orifice 56 (an elevated mouth) at top front 76 and outlet orifice 58 (a descending mouth) at bottom rear 78 of storage bag 54. Means 80 (shown in FIG. 5) secures urine intake orifice 56 to drain tube 62.

plug means 60, shown as a generally flat pliable key for urine outlet 58, includes serrated shaft 92 adapted to innerfit descending mouth 58. T-shaped crown 94 includes aperture 96 to receive flexible elastic ring 98, threaded through aperture 96 to effect a leakproof closing for outlet 58. Serrated shaft 92 is inserted into outlet 58 and elastic ring 98 is wrapped around outlet 58. Drain tube 62 is shown to include spool stops 72, spool 66 for rotatable strap 64, and mating means 20. These parts are discussed in relation to FIG. 8.

Referring now to FIG. 5, an enlargement of means 80 is shown. Means 80 is used to secure the urine storage bag to the drain tube as shown approximate point 56 in FIG. 4. Means 80 includes channeled, funnel shape shank 82 with concentric outer saw-toothed rings 84 and extended lip 86.

Referring now to FIGS. 4 and 5 in combination, means 80 has been inserted into orifice 56 with lip 86 descending into body 88 of urine storage bag 54. Elevated mouth 56 is adapted to surround shank 82 and to secure it therein by adjoining tether 90 (shown in FIG. 6) of bag 88.

Referring now to FIG. 6, a partial enlargement more clearly shows tether 90. Tether 90 is permanently attached to urine storage bag 88 at elevated mouth 56. Tether 90 terminates in a bonding surface at 91. As shown in FIG. 4, means 80 has been inserted into bag 88 and tube 62, and is secured to bag 88 by tether 90 and its bonding surface 91.

Referring now to FIG. 7, an enlargement vent plug 60 is shown as a generally flat pliable key including serrated shaft 92 and T-shaped crown 94 with aperture 96. Flexible elastic ring 98 is threaded through aperture 96 and around descending mouth 58 of storage bag 54 (as shown in FIG. 4) to effect a leakproof closing.

Referring now to FIG. 8, a schematic front view of apparatus 10 is shown worn by user 44. User 44 has donned, and adjusted to his size, elastic abdominal belt 46 around waist 48 via a tensioned grip buckle (not shown) and excess may be cut and discarded. Adjustable suspension belt 50 has been mounted on abdominal belt 46 at the area of anchor means 52. Suspension belt 50, adjusted to size by user 44, has been presized to span from abdominal belt 46 through harness 40 and returned to be anchored to abdominal belt 46 at anchor means 52, thereby supporting apparatus 10 with the male organ being encased by sheath 12 at a comfortable and unobtrusive position by strap 24 being wrapped around tunnel 12 and secured to cleat 30 by ring 28. Excess portions of suspension belt 50 may be cut and discarded by user 44.

Urine storage bag 54, with intake urine orifice 56 and outlet urine orifice 58 including plug means 60, has been mated to penile sheath 12 via flexible drain tube 62. Freely rotatable strap 64 surrounding loosely fitting slide spool 66 is adapted to mate with thigh belt 68, which may be mounted on either thigh, to aid in the positioning and angling of drain tube 62 between the legs 70 (one shown) of user 44. Spool 66 slides readily up and down drain tube 62 to prevent kinking of drain tube 62 whether user 44 sits, bends, kneels or lies down. Tight fitting spool stops 72 have been fitted over drain tube 62, near termini of drain tube 62, to prevent spool 56 from becoming locked on tumences in drain tube 62 at points of insertion in tube of friction coupling 20 and coupling 82 (not seen) at intake urine orifice 56.

In use, apparatus 10 is secured to user 44 by belts 46, 50 and 68. Penile sheath 12 is secured to a male organ by strap 24, intermediate ferrule 16 and cleated ferrule 22. Urine evacuated by user 44 is transferred from sheath 12 through drain tube 62, and collected into urinary storage bag 54 without leakage or backflow. It should be appreciated that penile sheath 12 can be utilized without the aforesaid drainage part of the apparatus and simply emptied by the user whenever desired. Most users, however, would likely prefer the body worn drainage system and at any time desired (and to avoid excess urine storage) to discharge urine they've accumulated in storage bag 54.

There are many variations which may be practiced and still be within the scope of this invention. While a ring and corresponding cleats are illustrated, any suitable means to secure the strap to the collar would remain within the scope of the invention.

The drain tube ends have been illustrated as discrete barrels. Any connector means that satisfies the intended use would still be within the scope of the invention.

Furthermore, while a belt and harness means are illustrated, any means which suspends the encased penis at a comfortable and unobtrusive angle and level would remain within the scope of the invention.

Still further, where the belts (abdominal suspension and leg) are fully detailed and illustrated, any suitable adjustments would still be within the scope of the invention.

While the breather pipe and belts are in the preferred embodiment, they are not critical to the device of this invention.

Again, while the preferred shape of the penile sheath and urine storage bag are illustrated, their shape is merely to be considered as a preference and not critical to the scope of this invention.

Finally, while the vent plug means has been illustrated as a key, any such means which accomplishes the intended purpose would still be within the scope of this invention.

There are many advantages to the apparatus of this invention. For example, the penile sheath has a universal sizing capability to snuggly, yet comfortably, fit any male penis and prevent the problem of backflow, malodor, anatomical damage, functional impairment and possible future infection.

The apparatus of this invention can be easily and safely mounted and used for extended time periods.

Likewise, the outer ferrule and cleated ferrule, cooperating with the strap, creates folds only within the tunnel. The core is, therefore, allowed to become and remain a comfortable, spacious ventilated hood.

The optional seaming of the sheath sides, if utilized, enhances side-to-side flex, providing maximum comfort, and reduces embarassing visibility in the cloth of the user's leg.

The apparatus of this invention provides an economical, discardable urine storage facility that precludes the necessity or impulse to continue the use of an expensive urine storage facility that is overage, noxious and embarassing, or which has become medically unacceptable.

The urine storage bag plug means allows easy and direct voiding into a toilet whenever this is desired.

The flexible drain tube, thigh strap and sliding apparatus inhibits the possibility of kinking of the drain tube and embarassing exposure, while simultaneously providing stability in the position of the urine storage bag.

Finally, the apparatus of this invention may be coupled with hospital appliances or facilities from either the discharge end of the sheath, the terminus of the drain tube, or the discharge orifice of the urine bag.

Having now illustrated and described our invention, it is not intended that such description limit the invention, but that the invention be limited only by a reasonable interpretation of the appended claims.

What is claimed is:

1. A body worn urinary collection system for a male incontinent, said apparatus comprising:
   (a) a reusable, generally moistureproof and pliable penile sheath shaped as an open ended sack and sized to loosely overfit the male organ, said sack including a first oversized, resilient, outer ferrule integral with and rimming said sack's open end to aid in mounting said sheath and a second resilient, cleated ferrule proximate said sheath's middle, said second cleated ferrule forming a tunnel to hold said mounted sheath spaced apart from the penis; and,
   (b) means to releasably secure said sack to said male organ proximate its intersection with the body, said means including a strap, one end of which is attached to said sack between said first outer ferrule and said second cleated ferrule and the other end of said strap terminating in a ring.
   so that when said sheath is worn, said first ferrule permits ease of donning and said second ferrule's cleats and said stop's ring together provide adjustable closing means.

2. The apparatus according to claim 1 wherein said sheath is comprised of two longitudinal halves, said halves being rim seamed together, said seam thereby providing a front and a rear demarcation for said sheath to enhance its side-to-side flexibility.

3. The apparatus according to claim 1 wherein said second cleated ferrule also includes, additionally, a harness.

4. The apparatus according to claim 1 wherein said sack's closed end terminates in a cone, said cone being generally at right angles to said sack's body and said urine outlet is located in said cone's apex.

5. The apparatus according to claim 1 wherein said device comprises, additionally, a harness mounted on said second ferrule, an adjustable abdominal belt sized to adjustably surround the user's waist and an adjustable suspension belt mounted on said abdominal belt and user-sized to span from said abdominal belt to link with said harness to hold the encased male organ in a suitably functioning, comfortable and unobtrusive position.

6. The apparatus according to claim 5 wherein said abdominal belt is elastic and releasably secured by a tension grip buckle.

7. The apparatus according to claim 5 wherein said abdominal belt includes an anchoring means to secure said suspension belt to said abdominal belt to be adjustably positioned at the abdomen.

8. The apparatus according to claim 7 wherein one end of said suspension belt is attached to said abdominal belt proximate said anchoring means, and the other end of said suspension belt terminates in an anchor.

9. A body worn urinary collection system for a male incontinent, said apparatus comprising:
(a) a reusable, generally moistureproof and pliable penile sheath shaped as a sack with both an open end and a closed end, said sack sized to loosely overfit a male organ, said sack's open end including a first oversized, resilient, outer ferrule integral with and rimming said sack's open end to aid in mounting said sheath, said sheath also including a urine outlet located proximate the closed sack end;
(b) means to releasably secure said sack to a male organ proximate its intersection with the body;
(c) a generally pliable and waterproof urine storage bag including an intake urine orifice and an outlet urine orifice, said outlet orifice including plug means;
(d) a thigh strap;
(e) a flexible drain tube, said drain tube being of a user-determined length to span from said sheath urine outlet to said storage bag intake urine orifice;
(f) means to attach said tube ends, one each to, respectively, said sheath urine outlet orifice and said storage bag intake urine orifice;
(g) a spool slidably mounted on said drain tube;
(h) a strap mounted at one end on said spool; and,
(i) a double faced engaging pad mounted on said strap's other end and releasably attached to said thigh strap to aid in the positioning and angulation of said drain tube between the user's legs,
so that when said sheath is worn secured to the penis, urine evacuated by the user is collected and transferred from said sheath through said drain tube and collected into said urinary storage bag without leakage or backflow.

10. The apparatus according to claim 9 wherein said sheath also includes a second resilient, cleated ferrule proximate said sheath's middle, said ferrule forming a tunnel to hold said mounted sheath spaced apart from the penis, and wherein said securing means is a strap, one end of which is attached to said sheath between said ferrule and said second cleated ferrule, the other end of said strap terminating in a ring adapted to mate with said cleats.

11. The apparatus according to claim 10 wherein said second cleated ferrule includes, additionally, a breather pipe located thereon and through said ferrule and said sheath to provide ventilation for said sheath.

12. The apparatus according to claim 11 wherein said breather pipe includes a releasable cap.

13. The apparatus according to claim 9 wherein said means to secure said one and of said tube to said urine outlet orifice is a friction coupling sleeve.

14. The apparatus according to claim 9 wherein said means to secure said tube's other end to said intake urine orifice of said storage bag is a bored, funnel-shaped shank with concentric outer rings and an extended lip, said shank sized to innerfit said other end of said tube up to said lip.

15. The apparatus according to claim 9 wherein said drain tube includes a pair of spool stops, one each proximate an end of said drain tube, said stops to prevent said rotatable strap spool from interferring with said means to secure said tube to said urine outlet of said sheath and said intake urine orifice of said urinary storage bag.

16. The apparatus according to claim 9 wherein said plug means includes a generally flat, pliable key with a serrated shaft, said key including a T-shaped crown, said crown including an aperture to receive a flexible elastic ring of a suitable length to be threaded through said aperture of said crown and around said outlet orifice mouth to effect a leakproof closing.

17. The apparatus according to claim 9 wherein said urine storage bag is generally rectangular in shape.

18. The apparatus according to claim 17 wherein said means to attach said tube end to said storage bag intake includes a funnel-shaped shank ending in a lip and said intake urine orifice of said urine bag is a mouth sized to overfit said lip, said mouth including an adjoining tether of a predetermined length to surround said mouth securing it to said shank.

19. The apparatus according to claim 17 wherein said outlet orifice of said urine bag is a descending mouth at the bottom rear of said urine bag.

20. A body worn urinary collection system for a male incontinent, said apparatus comprising:
(a) a reusable, generally moistureproof and pliable penile sheath shaped as an open ended sack and sized to loosely overfit a male organ, said sack's open end including a first oversized, resilient, outer ferrule integral with and rimming said sack's open end to aid in mounting said sheath, said sheath also including a urine outlet located proximate the closed sack end and a second resilient, cleated ferrule proximate said sheath's middle, said second cleated ferrule including a plurality of spaced-apart cleats, said ferrule forming a tunnel to hold said mounted sheath spaced apart from the penis;
(b) a strap, one end of which is attached to said sheath between said first outer ferrule and said second cleated ferrule, the other end of said strap terminating in a ring which can be attached to said cleats;

(c) a generally pliable and waterproof urine storage bag including an intake urine orifice and an outlet urine orifice, said outlet orifice including vent plug means and wherein said bag includes means for mounting said bag to a user's thigh;

(d) a flexible drain tube of a user-determined length to span from said sheath urine outlet to said storage bag intake urine orifice and having means attaching ends of said tube to said outlet and said inlet;

(e) a harness mounted on said second ferrule; and, (f) an adjustable abdominal belt and an adjustable suspension belt, said abdominal belt sized to adjustably surround the user's waist and wherein said suspension belt includes means releasably attaching said suspension belt to said abdominal belt and user-sized to span from said abdominal belt to link with said harness to hold the encased male organ in a suitably functioning, comfortable and unobtrusive position.

21. A body worn urinary collection system for a male incontinent, said apparatus comprising:

(a) a reusable, generally moistureproof and pliable penile sheath shaped as a sack with a closed corn-shaped end and an open end at generally right angles to said closed end, said sack sized to loosely overfit the male organ and formed of two longitudinal seamed halves;

(b) a first oversized, resilient, outer ferrule integral with and rimming said sack's open end to aid in mounting said sheath and a second resilient, cleated ferrule proximate said sheath's middle, said second cleated ferrule forming a tunnel to hold said mounted sheath spaced apart from the penis, said sheath also including a urine outlet proximate its closed end;

(c) means to releasably secure said sack to said male organ proximate its intersection with the body, said means including a strap, one end of which is attached to said sack between said first outer ferrule and said second cleated ferrule and the other end of said strap terminating in a ring;

(d) a generally pliable and waterproof urine storage bag including an intake urine orifice and an outlet urine orifice, said storage bag outlet orifice including plug means;

(e) a thigh strap;

(f) a flexible drain tube having means for mounting said tube on either of a user's thighs, said drain tube being of a user-determined length to span from said sheath urine outlet to said storage bag intake urine orifice;

(g) means to attach said tube ends, one each to, respectively, said sheath urine outlet orifice and said storage bag intake urine orifice;

(h) a spool slidably mounted on said drain tube;

(i) a strap mounted at one end on said spool; and, (j) a double faced engaging pad mounted on said strap's other end and having means removably attaching said pad to said thigh strap to aid in the positioning and angulation of said drain tube between the user's legs, so that when said sheath is worn, said first ferrule permits ease of donning and said second ferrule's cleats and said strap's ring together provide adjustable closing means and wherein urine evacuated by the user may be collected and transferred from said sheath through said drain tube and collected into said urinary storage bag without leakage or backflow.

* * * * *